United States Patent [19]

Pittner et al.

[11] Patent Number: 5,246,846
[45] Date of Patent: Sep. 21, 1993

[54] PROCESS FOR IMMOBILIZING PROTEINS ON A SUPPORT CONTAINING AMINO, MERCAPTO OR HYDROXY GROUPS

[76] Inventors: Fritz Pittner, Khekgasse 40-42/11, A-1235 Vienna; Thomas Schalkhammer, Gabelsbergerstrasse 5, A-3100 St. Pölten; Gerald Urban, Rembrandtstrasse 19/8, A-1020 Vienna; Eva Mann-Buxbaum, Ulmenstrasse 25, A-1140 Vienna, all of Austria

[21] Appl. No.: 613,810
[22] PCT Filed: Apr. 4, 1990
[86] PCT No.: PCT/AT90/00026
§ 371 Date: Dec. 31, 1990
§ 102(e) Date: Dec. 31, 1990
[87] PCT Pub. No.: WO90/12092
PCT Pub. Date: Oct. 18, 1990

[30] Foreign Application Priority Data

Apr. 4, 1989 [AT] Austria .................................. 786/89
May 10, 1989 [AT] Austria .................................. 1119/89

[51] Int. Cl.$^5$ ..................... C12N 11/00; C12N 11/14; G01N 33/551; G01N 33/553
[52] U.S. Cl. .................................... 435/174; 435/176; 435/181; 436/524; 436/525; 436/532; 530/811; 530/816
[58] Field of Search ............... 435/174, 176, 177, 180, 435/181; 436/524, 525, 532; 530/811, 816

[56] References Cited

U.S. PATENT DOCUMENTS 4,229,537 10/1980 Hodgins et al. ..................... 435/177

FOREIGN PATENT DOCUMENTS 777041 4/1978 U.S.S.R. .
2163434 2/1986 United Kingdom .

OTHER PUBLICATIONS

Brandt, et al., Biochimica et Biophysica Acta, vol. 386, 1975, pp. 196-202.
"Immobilized Enzymes," Methods in Enzymology, vol. XLIV, Klaus Mosbach, pp. 134-149, 1976, Academic Press, N.Y.

Primary Examiner—David M. Naff
Attorney, Agent, or Firm—Nixon & Vanderhye

[57] ABSTRACT

Reactants containing amino, mercapto or hydroxy groups such as proteins, peptides, ligands, coenzymes or enzymes are immobilized on a support containing amino, mercapto or hydroxy groups by coupling the reactant to the support with a compound having the following formula (I) or (IA):

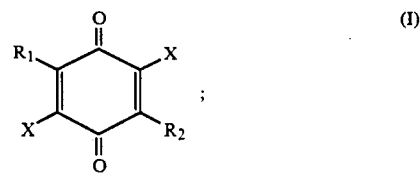

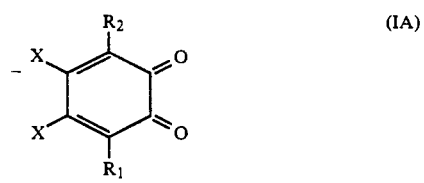

wherein X is a halogen and $R_1$, $R_2$ are the same or different and are X, R, COR, COOR, wherein R is $C_1$-$C_8$ alkyl, COOH, CNS, $N_3$ or CN. The support may be first reacted with the compound to produce a derivatized support which is then reacted the reactant or the reactant may be first reacted with the compound and the resultant product then reacted with the support. An electrochemical biosensor can be prepared by using a conductive support.

17 Claims, No Drawings

PROCESS FOR IMMOBILIZING PROTEINS ON A SUPPORT CONTAINING AMINO, MERCAPTO OR HYDROXY GROUPS

The invention relates to a process for immobilizing proteins, peptides, ligands, coenzymes, redox mediators or the like on a support, which exhibits amino, mercapto or hydroxy groups. Such immobilizates, i.a., are known as enzyme immobilizates, which can be used in bioreactors or in the area of biosensory function. Enzyme immobilizates of the initially mentioned type contain, for example, beta-glucosidases, lipases, esterases, phosphatases, oxireductases or naringinases and are used for processing of food, purification of waste water, biocatalyzed organic syntheses, bioanalytics and medical techniques. With now known and used immobilization methods the number and spatial distribution of the reactive groups suitable for coupling can be controlled only in rare cases and only inadequately. Also in most cases it is not possible to activate support materials with amino, mercapto or hydroxy groups with a single process. Also the storage of the activated support material is not possible in most processes.

Immobilizates of the initially mentioned type are produced mostly with the use of glutardialdehyde, and then depending on the type of support, the support has to be derivatized if it exhibits primary amino groups, which later are reacted with glutardialdehyde and still later with the proteins, peptides, coenzymes or the like to be immobilized. Derivatized supports, which are reacted with glutardialdehyde, cannot be dried without loss of activity.

The object of the invention is to provide a process of the initially mentioned type, in which a derivatized support, with amino but also mercapto and hydroxy groups, after a coupling, can be directly reacted with the proteins, peptides, ligands, coenzymes or the like to be immobilized, can be dried without loss of activity, and with which even thin layers of proteins, peptides, coenzymes or the like, especially monolayers, can be immobilized at the same time with high mechanical stressability. To achieve this object, the process according to the invention essentially consists in the fact that the support is reacted with a compound of general formula (I) or (IA)

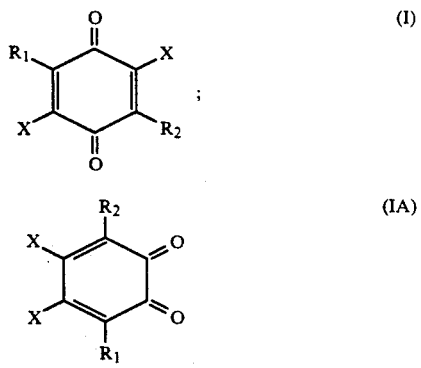

in which X means halogen and $R_1$, $R_2$ are the same or different and mean X, R, COR, COOR, in which R means $C_1$-$C_8$ alkyl, COOH, CNS, $N_3$ or CN, and optionally is dried, after which the peptides, proteins, coenzymes or the like to be immobilized are reacted with the free halogen—in ortho or para position to the C=O group—of the compound of general formula (I) or (IA). In this case, the compound of general formula (I) or (IA)) first forms by substituent X a covalent bond with the amino, mercapto or hydroxy groups of the support by which an especially stable coupling is achieved. Now the second substituent X, activated by the first coupling, can be reacted with the amino, hydroxy or mercapto groups of the reactant to be immobilized, and an especially stable covalent coupling is achieved. The coupling reaction between the compound of general formula (I) or (IA) and the support or the compound to be immobilized to a high degree is very dependent on the reactivity of the respective substituents. Thus with the compounds of general formula (I) or (IA) in which $X = R_1 = R_2$ the reactivity according to the following series is decreasing $X = F$, Cl, Br > I, $N_3$, COOH, COR, COOR, $NO_2$ > CN, CNS, R, and R means $C_1$-$C_8$ alkyl. The preferred substituents of the compounds of formula (I) or (IA) therefore are fluorine, chlorine and bromine. Therefore the coupling of o-chloranil or o-bromanil with an amino support material such as, for example, aminosilylated metal or glass surfaces can be considered as model reaction. Also the reactivity of the support is dependent on the respective substituents and decreases corresponding to the following series $NH_2$ > NH, SH >> OH.

The reactivity of the support material thus activated is clearly greater for the coupling of amino and mercapto groups than that for the coupling of hydroxy groups. Therefore most preferred is the reaction of a support which carries a primary amino group with a compound of formula I, in which the substituents X, $R_1$ and $R_2$ are the same and each mean fluorine, chlorine or bromine.

The free halogen, in the ortho or para position to a carbonyl group, subsequently can again, by formation of covalent bonds can be reacted with amino groups, hydroxy groups or optionally mercapto groups of the proteins, peptides, coenzymes or the like to be immobilized with formation of covalent bonds, by which monolayers can easily be produced with high mechanical bearing capacity. The number and spatial arrangement of the reactive groups in this case can be controlled by the photochemical reaction so that also the specific arrangement of different monolayer structures on a support or the specific immobilization of multilayer coatings is possible. The reaction of the coupling agent with the proteins, peptides, coenzymes or the like is also dependent on the respective reactive groups of proteins, peptides and coenzymes or the like. In the reaction of these compounds in water or in buffer solutions the following reactivity series occurred $NH_2$ > NH ~ SH >> OH The use of a compound of general formula (I) or (IA) for the immobilization of proteins, peptides, coenzymes, ligands or the like on a support further offers the advantage that the compound of general formula (I) or (IA) in an especially simple way can be deactivated over specific areas of the surface of the support. The deactivation can be performed in a simple way by photochemical reaction or by reaction with bases, by which especially with selective photochemical deactivation extremely small components can be produced with the desired coupling activity. Such small components are suitable subsequently, for example, also for use as biosensors, but also for chemical and biochemical detection systems on a test strip basis or the like.

The usual supports for the production of immobilizates are suitable in this case as supports, and especially conductive layers or conductive supports made from metals, such as, for example, gold, platinum, palladium, rhodium or carbon are suitable for use as electrochemical biosensors.

In an especially advantageous way in the framework of the process according to the invention, 2,3,5,6-tetrachlorocylohexadiene-1,4-dione can be used for immobilization as the compound of formula (I) and 3,4,5,6-tetrabromocyclohexadiene-1,2-dione or 3,4,5,6-tetrabromocylohexadiene-1,2-dione can be used for immobilization as the compound of formula (IA). The additional substituents, such as other halogen atoms, COOH, COR, COOR, CNS, $NO_2$, $N_3$ or CN, which are known as deactivating substituents in electrophilic substitution of aromatic substances, further activate the para halogen atoms participating in the coupling reaction between supports and the proteins, peptides, coenzymes, ligands or the like so that an especially stable covalent bond can be achieved. This transactivation for the coupling of the support with the substances to be immobilized can be appropriately controlled by choice of the other substituents, especially by the choice of halogen, such as Cl, Br or groups such as, e.g.,

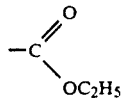

and activity improvements can be achieved by appropriate steric alignment of the substances to be immobilized.

In an especially simple way the reaction of the support with compounds of general formula (I) or (IA) can be performed in organic or organically aqueous mixed phases, and the reaction of the support with the compounds of general formula (I) or (IA) in anhydrous organic solvents, especially toluene, is especially preferred. Especially the reaction of the compound of general formula (I) or (IA) with the support can easily be performed at increased temperatures for acceleration of the reaction, and the operation can be performed at temperatures between $-10°$ C. and reflux temperature, preferably $20°-70°$ C. For the immobilization of proteins, peptides, coenzymes, ligands or the like naturally the temperature has to be limited so that substances to be immobilized cannot be thermally denatured.

As proteins advantageously within the framework of the process according to the invention, redoxenzymes, such as, e.g., glucoseoxidase, galactoseoxidase, amino acid oxidase, xanthinoxidase, cholesteroloxidase, uricase and ascorbatoxidase or their apoenzymes, can be used. Such redoxenzymes are especially suitable for the production of biosensors, and the corresponding enzyme-catalyzed redox reaction, which the redoxenzymes bring about, can be measured electrochemically by subsequent products, e.g., $H_2O_2$. In this way, miniaturized biosensors for blood sugar determination with the use of glucoseoxidase can be produced. The freshness of foods, such as, for example, fish, can be determined with biosensors on the basis of xanthinoxidase in an especially simple way. Analogously, a series of biosensors can be produced with such redoxenzymes, and for the production of such biosensors as a special advantage of the use of the compound of general formula (I) or (IA) the fact is added that partial areas of the surface of the support can be photochemically deactivated after reaction of the compound of general formula (I) or (IA). In this way, exactly defined reactive surfaces can be created, and especially also multilayer, microbuilding biosensors can be achieved, in which parts of the surface of different functions have differently selective sensitivity. For this purpose, advantageously the procedure can be followed so that the surface of the reaction product with the compound of general formula (I) or (IA) is partly deactivated by photochemical reaction or by use of alkaline reagents or low-molecular amines or thiols, after which the reaction with peptides, proteins, coenzymes, ligands or the like with the remaining parts of the surface is performed, and to achieve a multilayer or multifunctional biosensor in a simple way the procedure can be followed so that the immobilizate again is reacted with compound of general formula (I) or (IA), after which optionally after partial deactivation of the surface again peptides, proteins, coenzymes or the like are immobilized. For the production of a biosensor the immobilization advantageously takes place on a support provided with electrodes, and for the further increase of the mechanical bearing capacity advantageously the procedure can be followed that the immobilizate for the use as a biosensor can be provided with a physiologically compatible cover layer, especially a negative space charge.

Especially the design of an outside of the cover layer with a negative space charge has the advantage here that the side reactions interfering with the determination can be suppressed. Thus especially the glucose determination with glucoseoxidase is interfered with by ascorbate and citrate, and a negative charge of the outside of a cover layer counteracts a penetration of such anions and in this way a distortion of the measured values is avoided.

The use of the compound of general formula (I) or (IA) for the production of biosensors in the above sense in this case has the substantial advantage, in comparison with other methods of immobilization, especially in comparison with an immobilization with glutardialdehyde, that the coupling layer shows redox activity, so that the compound of general formula (I) or (IA) can be used as redox-transmitting intermediate layer for transmission of electrons. In this way, the sensitivity of a biosensor, produced with the use of a compound of general formula (I) or (IA), is substantially increased. The compounds of formula (IA), namely o-quinones are usable by their redox activity for electron transfer between redoxenzymes and the electrode surface. Moreover, the o-quinone structure can be coupled with aromatic o-diamines to phenazine structures, which are also suitable as redox mediators for the electron transfer between electrode and cofactors.

Besides the use of the immobilizates, produced according to the invention, for the production of biosensors, immobilizates can also be produced for diagnostic purposes, such as, for example, tests strips, immunosensors so that antigens or antibodies are used for immobilization. Finally, with respect to the especially high mechanical stability of the immobilizate, it is also possible to produce immobilizates to be used biotechnologically in bioreactors, fermenters, bioorganic syntheses, and preferably alpha- or beta-glucosidases, glycosidases, galactosidases, lipases, pectinases, esterases, penicillininase, ammonialysases, urease and/or phosphatases are used. Such immobilizates are suitable for the bioprocess technique, food technique, sewage and environmental technology.

To achieve multilayers it has proven to be especially advantageous to perform the process so that proteins, peptides, coenzymes or the like are reacted with an at least equimolar amount of a compound of formula (I) or (IA)

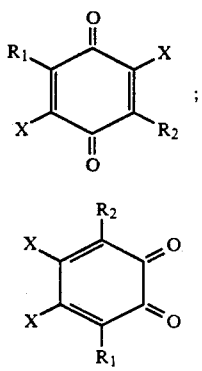

in which X means halogen and $R_1$, $R_2$ are the same or different and mean X, R, COR, COOR, in which R means $C_1$-$C_8$ alkyl, COOH, CNS, $N_3$ or CN, and optionally are dried, after which the reaction product obtained is coupled with the support by a free halogen—in ortho or para position to the C=O group—of the compound of formula (I). By reaction of a compound of formula (I) or (IA) with proteins, peptides, coenzymes, ligands or the like it is possible, by bridging the compound of formula (I) or (IA), to obtain crosslinked proteins, peptides or the like, which can be bound on the support by a free, uncrosslinked para-position halogen. In this way, it is possible to obtain directly in one reaction step multilayers of enzymes immobilized on a support.

Within the framework of the process according to the invention it is also possible to reverse the activation steps and first to react the proteins, peptides, ligands, effectors, which exhibit amino, mercapto or hydroxy groups, with a compound of general formula (I) or (IA) and then bind the thus activated molecules on a support. By the bifunctional properties of the compound of general formula (I) or (IA) proteins, peptides, ligands or the like are crosslinked to polymer macromolecules, which can also be used in the form as immobilizates, which can then be additionally bound with the free reactive groups on a support material. For special problems, another macromolecule can also be used as support material, such as, for example, a dextran, xanthan, polyethylene glycol, polyethylenimine, support protein or the like. By the choice of the reaction conditions the degree of polymerization and of the immobilization type can be controlled.

The invention in explained in greater detail below by embodiments.

EXAMPLE 1

Derivatizing Microporous Glass

A. Aqueous Silanizing 100 g of microporous glass is mixed with a 10% aqueous 3-(triethoxysilyl) propylamine solution. Within the first 30 minutes the pH of the reaction solution must be constantly controlled and adjusted to pH 3.5. This batch is stirred for 4 hours at room temperature. Then the microporous glass is separated from the reaction solution and washed 5 times with 100 ml of water each and dried at 110° C.

B. Organic Silanizing 100 g of microporous glass is mixed with a 10% 3-(triethoxysilyl) propylamine solution. This batch is stirred for 5 hours at room temperature. Then the silanized microporous glass is separated from the reaction solution and washed 5 times with 50 ml of toluene each.

C. Activation a) The microporous aminated glass, produced according to process A or B, is mixed with a 2.5% 2,3,5,6-tetrachlorocyclohexadiene-1,4-dione toluene solution and stirred for 30 minutes at 40° C. After the completion of the reaction, the glass is separated from the reaction solution and washed 5 times with 50 ml of toluene each and 2 times with 100 ml each of acetone. Then the derivatized microporous glass is suctioned dry with a water-jet vacuum and stored in this state.

The derivatizing of the silanized surfaces was also performed by use of 2,3,5,6-tetrabromo- or 2,3,5,6-tetrafluoro-or 2,3,5,6-tetraiodo-cyclohexadiene-1,4-dione.

b) The microporous aminated glass, produced according to process A or B, is mixed with a 2% 3,4,5,6-tetrachlorocyclohexadiene-2,1-dione solution in toluene and mixed thoroughly for 30 minutes at 25° C. After the completion of the reaction, the glass is separated from the reaction solution and washed 5 times with 50 ml of toluene each and 2 times with 100 ml each of acetone. Bright light irradiation and increased temperatures are to be avoided during the activation and also after that as long as it is not yet coupled. Then the derivatized microporous glass is dried in the water-jet vacuum and stored in this state with exclusion of light at 4° C.

The derivatizing of the silanized surfaces was also performed with the use of 3,4,5,6-tetrabromocyclohexadiene-1,2-dione or 3,4,5,6-tetrafluorocyclohexadiene-1,2-dione.

EXAMPLE 2

Derivatizing Platinum, Palladium or Rhodium Surfaces

A. Chemical Oxidation of the Surfaces

The Pt, Pd or Rh surfaces are placed in a 15% aqueous $HNO_3$ solution at room temperature for 20 hours and then washed several times with water.

B. Electrochemical Oxidation of the Surfaces

The Pt, Pd or Rh surfaces are oxidized in an aqueous 10% $HNO_3$, 2.5% $Cr_2O_7$ solution for 15 seconds under vigorous oxygen evolution.

C. Silanizing and Activation

The Pt, Pd or Rh surfaces, oxidized according to process A or B, are flushed several times with acetone, dried at room temperature and then placed in a 10%

3-(triethoxysilyl) propylamine toluene solution for 30 minutes at 60° C.

a) The silanized surfaces are then washed with toluene and placed for 30 minutes in a 2% 2,3,5,6-tetrachlorocyclohexadiene-1,4-dione toluene solution at 40° C. After completion of the reaction, the surfaces are flushed several times with toluene and finally with acetone. The derivatized Pt or Pd surfaces are stored in the dry state with exclusion of light.

b) The silanized surfaces are washed with toluene and dried for 20 minutes at 110° C. Then the aminated metal surfaces are placed in a 2% solution of 3,4,5,6-tetrachlorocyclohexadiene-1,2-dione in toluene and left in it for 20 minutes at 25° C. After completion of the reaction, the electrodes are flushed with acetone and stored with exclusion of light at 4° C. During the entire activation process the operation must be performed with strongly attenuated light, best red light.

EXAMPLE 3

Derivatizing Porous Silicate Material 100 g of porous silicate material is mixed with a 10% 3-(triethoxysilyl) propylamine toluene solution. This batch is stirred for 1 hour at 60° C. Then the silanized porous silicate material is separated from the reaction solution and washed 5 times with 50 ml of toluene each.

a) Then the porous silicate material is mixed with a 1.5% 2,3,5,6-tetrachlorocyclohexadiene-1,4-dione toluene solution and stirred for 30 minutes at 40° C. After completion of the reaction period the silicate material is separated from the reaction solution and washed 5 times with 50 ml of toluene each and 2 times with 100 ml of acetone each. Then the derivatized silicate is suctioned dry with a water-jet vacuum and stored in this state.

Derivatizing the porous silicate material was also performed with use of 2,3,5,6-tetrabromocyclohexadiene-1,4-dione, 2,3,5,6-tetraiodocyclohexadiene-1,4-dione.

b) Then the porous silicate material is mixed with a 1% 3,4,5,6-tetrachlorocyclohexadiene-1,2-dione solution in toluene and stirred for 30 minutes at 25° C. After completion of the reaction, the silicate material is separated from the reaction solution and washed 5 times with 50 ml of acetone each. Then the derivatized silicate is dried in a water-jet vacuum and stored in this state with exclusion of light at 4° C.

The derivatizing of the silanized surfaces was also performed with the use of
3,4,5,6-tetrabromocyclohexadiene-1,2-dione or
3,4,5,6-tetrafluorocyclohexadiene-1,2-dione.

EXAMPLE 4

Photodeactivation of 2,3,5,6-tetrachloro- or
2,3,5,6-tetrabromo-or 2,3,5,6-tetrafluoro- or
2,3,5,6-tetraiodocyclohexadiene-1,4-dione as well as
3,4,5,6-tetrachloro or 3,4,5,6-tetrafluoro or
3,4,5,6-tetrabromocyclohexadiene-1,2-dione
derivatized surfaces The derivatized metal surfaces, after covering with a photomask, were exposed to an intensive UV irradiation in the region of the absorption bands of a wavelengths of 200–600 nm for 1 second to 30 minutes. Then the glucoseoxidase was coupled. The activity of the glucoseoxidase was measured amperometrically. In this case it was shown that the irradiated spots of the surface exhibit a deactivation of the coupling groups proportional to the amount of light. The amount of the coupled glucoseoxidase was smaller by a value proportional to the amount of light.

EXAMPLE 5

Immobilization on Surfaces Derivatized With Compounds of Formula (I)

The derivatized support materials are incubated with 5 (w/w) of the protein to be immobilized in 10–20 times the amount of a suitable buffer at a pH in the range of 4–9 for 2 hours at room temperature. The immobilizate was freed of the adsorbing protein by washing with different buffers.

A

A naringenase immobilizate starting from native naringenase with 1 nkat/mg exhibited an activity of 5.5 nkat/g of immobilizate.

B

A phosphatase immobilizate starting from native alkaline phosphatase with 0.25 nkat/mg exhibited an activity of 2 nkat/g of immobilizate.

C

A beta-galactoxidase immobilizate starting from native beta-galactoxidase with 0.68 nkat/mg exhibited an activity of 4.6 nkat/g of immobilizate.

D

Technical lipase from Candida cylindracea showed the same synthetase and hydrolase activity as comparable immobilizates with glutardialdehyde but of small clumping behavior in organic solvents.

E

The activity of glucoseoxidase immobilized on metal surfaces corresponded to an impermeable monomolecular enzyme layer.

EXAMPLE 6

Immobilization on Surfaces Derivatized with Compounds of Formula (IA)

The derivatized support materials are incubated with 15 (w/w) of the protein to be immobilized in 10–20 times the amount of a suitable buffer at a pH in the range of 4–9 for 2 hours at 4°–25° C. The immobilizate was freed of the adsorbing protein by washing with different buffers.

A

A glucuronidase immobilizate, starting from native glucuronidase with 300 nkat/g, exhibited an activity of 22 nkat/g of immobilizate. The protein content was 51 mg/g of support.

B

An alkaline phosphatase immobilizate, starting from native phosphatase with 26 kat/g, exhibited an activity of 420 nkat/g of immobilizate. The protein content was 20.6 mg/g of support.

C

A beta-galactosidase immobilizate, starting from native galactosidase with 7.6 kat/g, exhibited an activity of 43 nkat/g of immobilizate.

We claim:

1. A process for immobilizing a reactant on a support having amino, mercapto or hydroxy groups comprising
   (i) reacting a support having an amino, mercapto or hydroxy group with a compound having the formula (I) or (IA)

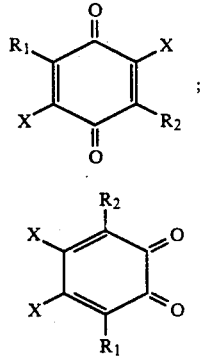

wherein X is a halogen and $R_1$, $R_2$ are the same or different and are X, R, COR, COOR, wherein R is $C_1$-$C_8$ alkyl, COOH, CNS, $N_3$ or CN to form a derivatized support, and
   (ii) reacting a reactant to be immobilized having an amino, mercapto or hydroxy group with the halogen in ortho or para position to the C=O group of said derivatized support.

2. A process according to claim 1, wherein said compound of formula (I) is 2,3,5,6-tetrachlorocyclohexadien-1,4-dione.

3. A process according to claim 1, wherein said compound of formula (IA) is 3,4,5,6-tetrachlorocyclohexadien-1,2-dione or 3,4,5,6-tetrabromocyclohexadien-1,2-dione.

4. A process according to claim 1, wherein said reactant is a protein.

5. A process according to claim 1, wherein said reactant is a ligand.

6. A process according to claim 1, wherein said reactant is a coenzyme.

7. A process according to claim 1, wherein said reactant is a redox enzyme.

8. A process as in claim 1, wherein said derivatized support is dried prior to step (ii).

9. A process according to claim 1, wherein step (i) is performed in organic or organically aqueous mixed phases.

10. A process according to claim 9, wherein step (i) is performed in anhydrous organic solvents.

11. A process according to claim 1, wherein step (i) is performed at temperatures between $-10°$ C. and reflux temperature.

12. A process according to claim 1, wherein said reactant is a redoxenzyme selected from the group consisting of glucoseoxidase, galactoseoxidase, amino acid oxidase, xanthinoxidase, cholesteroloxidase, uricase and ascorbatoxidase and their apoenzymes.

13. A process according to claim 1, wherein said reactant is an antigen or antibody.

14. A process according to claim 1, wherein said reactant is a naringinase, alpha- or beta-glucosidase, glycosidase, galactosidase, lipase, pectinase, esterase, penicillininase, ammonialysase, urease or a phosphatase.

15. A process according to claim 1, further comprising after step (i) partially deactivating the surface of said derivatized support by photochemical reaction or by use of alkaline reagents or low-molecular amines or thiols.

16. A process according to claim 1, further comprising after step (ii) carrying out the steps of
   (iii) reacting the product of step ii) with said compound, and
   (iv) reacting a reactant to be immobilized having an amine, mercapto or hydroxy group with the halogen in ortho or para position to the C=O group of the product of step iii).

17. A process for immobilizing a reactant on a support having amino, mercapto or hydroxy groups comprising
   (i) reacting a reactant to be immobilized having an amino, mercapto or hydroxy group with a compound having the formula (I) or (IA)

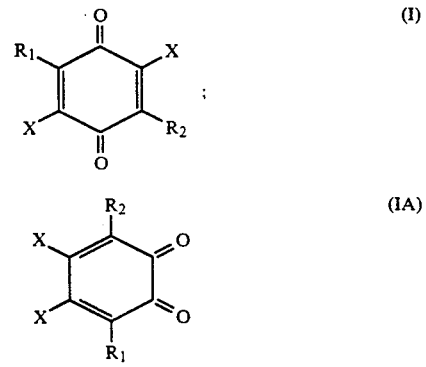

wherein X is a halogen and $R_1$, $R_2$ are the same or different and are X, R, COR, COOR, wherein R is $C_1$-$C_8$ alkyl, COOH, CNS, $N_3$ or CN, and
   (ii) reacting a support having an amine, mercapto or hydroxy group with the halogen in ortho or para position to the C=O group of the product of step i).

* * * * *